March 19, 1957 A. J. MILLER Plant Pat. 1,579
ROSE PLANT
Filed July 9, 1956
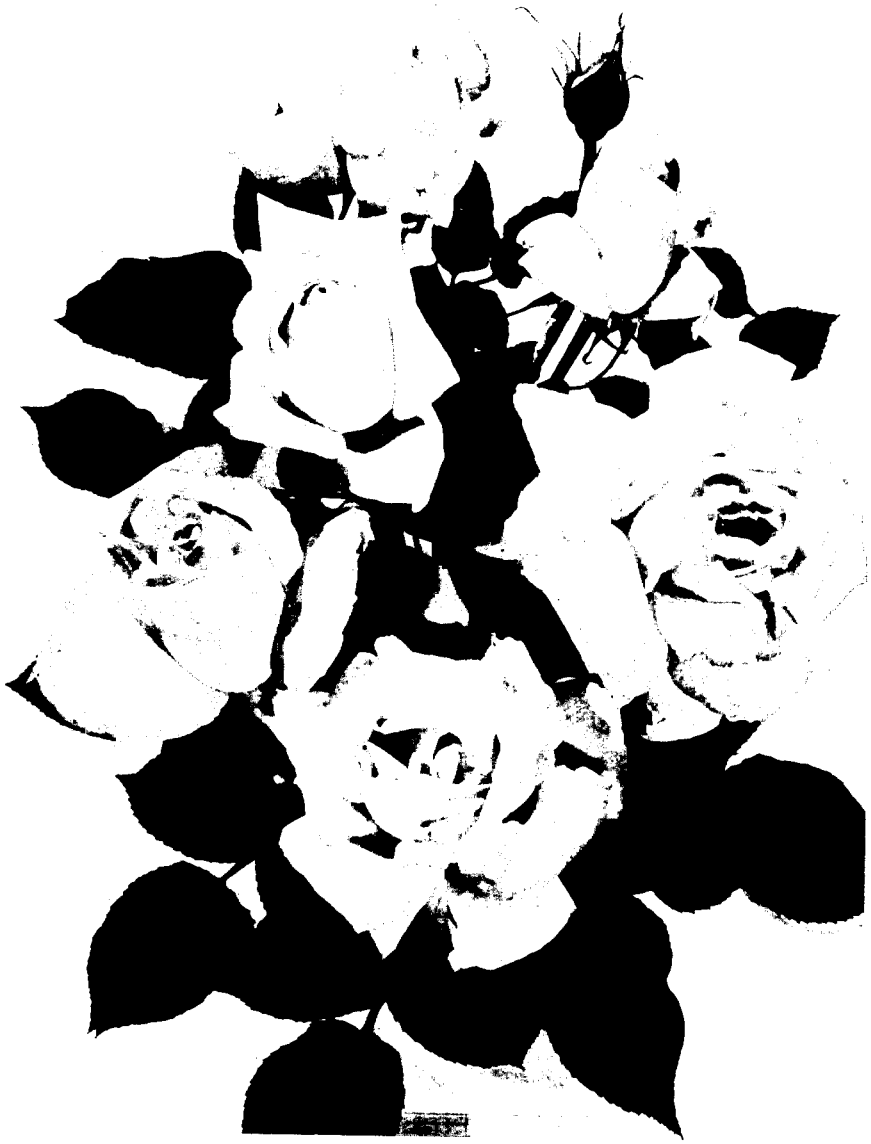
Inventor
A. J. Miller
By: Robbins & Cobb
Attorneys.

United States Patent Office

Plant Pat. 1,579
Patented Mar. 19, 1957

1,579

ROSE PLANT

Andrew J. Miller, Montebello, Calif., assignor to Constance A. Elmer, trading as Elmer Roses, San Gabriel, Calif.

Application July 9, 1956, Serial No. 596,810

1 Claim. (Cl. 47—61)

The present invention relates to a new and distinct variety of rose plant of the hybrid tea class, which was originated by me by crossing the variety "Tom Breneman" (Plant Patent No. 986) with the variety "Show Girl" (Plant Patent No. 646).

As the result of this breeding, I have produced a new rose variety whose flowers have a damask fragance that is exceedingly rare, and which is unique in the combination of this rare fragrance with a distinctive Rhodomine Pink general color tonality of the blooms.

The foregoing characteristics definitely differentiate my new variety from its parents, as well as from all other varieties of which I am aware, and asexual reproduction thereof as performed by me by budding at Montebello, California, shows that these characteristics and distinctions come true to form and are established and transmitted through succeeding propagations.

The accompanying drawings shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Type: Hardy; bush; outdoor; seedling; for cut flowers and for garden decoration.

Class: Hybrid tea.

Parentage: Seedling.

*Seed parent.*—"Tom Breneman."

*Pollen parent.*—"Show Girl."

Propagation: Holds its distinguishing characteristics through succeeding propagations by budding.

*Flower*

Locality where grown and observed: Montebello, California.

Continuity: Continuous.

Fragrance: Damask.

Flowers Borne: Sometimes singly, but sometimes 2 or 3 to a stem; in regular clusters; on long stems.

Quantity of bloom: Abundant, outdoors.

Bud:

*Peduncle.*—Long; medium caliper; stiff; smooth. Color—reddish green.

*Before calyx breaks.*—Size—medium. Form—short; without foliaceous appendages on the surface or beyond the tip of the bud. Color—Maize yellow, Plate 607/1.

*As calyx breaks.*—Color—Maize Yellow, Plate 607/2.

*As first petal opens.*—Size—large. Form—long. Color: outside—Rhodomine Pink, Plate 527/2; inside—Rhodomine Pink, Plate 527/2.

*Opening.*—Opens up well.

Bloom:

*Size (when fully opened).*—Large; from 4 to 4½ inches.

*Petalage.*—Double; from 30 to 35 petals.

*Form.*—Very high-centered at first, but becoming high-centered; petals being at first tightly rolled outward and remaining tightly rolled outward at maturity.

Petals:

*Texture.*—Thick; with both inside and outside satiny.

*Shape.*—Outside—ovate, with apex flat. Intermediate—ovate, with apex flat. Inside—ovate, with apex flat.

This description of a newly opened flower was made from a rose grown outdoors in the month of May, at Montebello, California:

*Color.*—Outer petal: outside surface—Rhodomine Pink, Plate 527/1; inside surface—Rhodomine Pink, Plate 527/1. Intermediate petal: outside surface—Rhodomine Pink, Plate 527/2; inside surface—Rhodomine Pink, Plate 527/2. Inner petal: outside surface—Rhodomine Pink, Plate 527/2; inside surface—Rhodomine Pink, Plate 527/2.

This description was made from a rose that was open for 3 days outdoors in the month of May, at Montebello, California:

*Color.*—Outer petal: outside surface—Rhodomine Pink, Plate 527/3; inside surface—Rhodomine Pink, Plate 527/3. Inner petal: outside surface—Rhodomine Pink, Plate 527/3; inside surface—Rhodomine Pink, Plate 527/3.

*General color effect.*—Newly opened flower—Rhodomine Pink, Plate 527/3. 3-days open—Rhodomine Pink, Plate 527/3.

*Behavior.*—Drop off cleanly; is not affected by cold, hot, wet or dry weather.

*Flower longevity.*—On bush in garden—5 days in May. Cut roses grown outdoors and kept at living room temperatures—3 days in June.

*Reproductive organs*

Stamens: Many; regularly arranged. Color—Buttercup Yellow, Plate 5/3.

Filaments: Long; many with anthers. Color—reddish.

Anthers: Large; all open at once. Color—yellow.

Pollen: Moderate. Color—yellow.

Pistils: Medium number.

Styles: Even; medium length; medium caliper; bunched.

Stigma: Color—white.

Ovaries: All enclosed in calyx.

Hips: Ovoid; smooth; with thin walls. Color—green.

Sepals: Permanent; long. Color—Scheele's Green, Plate 860/2.

Seeds: Few; small.

*Plant*

Foliage:

*Leaves.*—Compound of 5 leaflets; abundant; large; heavy.

*Leaflets.*—Shape—ovoid, with obtuse apex. Margin—serrate.

*Color.*—Mature: upper surface—dark green; under surface—light green. Young: upper surface—dark green; under surface—light green.

*Rachis (the supporting stem of the compound leaf).*—Medium caliper. Upper side—grooved. Under side—sparsely thorny.

*Stipules.*—Medium length; medium width; with long points turning out at an angle of about 90°; recurved toward the stem.

*Disease resistance.*—Good resistance to both mildew and blackspot, as determined by comparison with other varieties grown under comparable cultural conditions at Montebello, California.

Growth:

*Habit.*—Upright.

*Growth.*—Vigorous.

*Canes.*—Medium caliper.

*Main stems.*—Color—dull green and red. Thorns—straight; with narrow base. Prickles—none. Hair—none.

*Branches.*—Color—dull green and red. Thorns—few; medium length; straight; with narrow base. Prickles—none. Hairs—none.

*New shoots.*—Color—dull red. Thorns—few; medium length; straight. Prickles—none. Hairs—none.

I claim:

A new and distinct variety of rose plant of the hybrid tea class, substantially as herein shown and described, characterized particularly as to novelty by the unique combination of a rare damask fragrance and the distinctive Rhodomine Pink general color tonality of its blooms.

No references cited.